United States Patent [19]

Apelian et al.

[11] Patent Number: 5,242,676
[45] Date of Patent: Sep. 7, 1993

[54] SELECTIVE SURFACE DEALUMINATION OF ZEOLITES USING DICARBOXYLIC ACID

[75] Inventors: Minas R. Apelian, Vincetown, N.J.; Anthony S. Fung, Chadds Ford, Pa.

[73] Assignee: Mobil Oil Corp., Fairfax, Va.

[21] Appl. No.: 881,282

[22] Filed: May 11, 1992

[51] Int. Cl.$^5$ .............................................. C01B 33/34
[52] U.S. Cl. .................................... 423/714; 502/85; 502/60; 502/64; 502/77; 423/DIG. 22; 423/DIG. 23; 423/DIG. 29; 423/DIG. 30; 423/DIG. 35; 423/DIG. 36
[58] Field of Search ................ 423/326, 328, 329, 330, 423/700, 714, DIG. 22, DIG. 23, DIG. 29, DIG. 30, DIG. 35, DIG. 36; 502/60, 62, 64, 66, 77, 85, 86

[56] References Cited

U.S. PATENT DOCUMENTS

| | | | |
|---|---|---|---|
| 3,442,795 | 5/1969 | Kerr et al. | 208/120 |
| 4,002,697 | 1/1977 | Chen | 260/671 M |
| 4,088,605 | 5/1978 | Rollmann | 252/465 Z |
| 4,100,215 | 7/1978 | Chen | 260/671 M |
| 4,101,595 | 7/1978 | Chen et al. | 260/668 A |
| 4,278,564 | 7/1981 | Pelrine | 502/62 |
| 4,335,019 | 6/1982 | Bowes et al. | 502/66 |
| 4,388,177 | 6/1983 | Bowes et al. | 208/111 |
| 4,520,221 | 5/1985 | Chen | 585/517 |
| 4,533,533 | 8/1985 | Dewing et al. | 502/60 |
| 4,568,786 | 2/1986 | Chen et al. | 585/517 |
| 4,654,316 | 3/1987 | Barri et al. | 502/85 |
| 4,716,135 | 12/1987 | Chen | 502/62 |
| 5,043,307 | 8/1991 | Bowes et al. | 502/86 |
| 5,080,878 | 1/1992 | Bowes et al. | 423/328 |

FOREIGN PATENT DOCUMENTS

259526B1 3/1989 European Pat. Off. .

Primary Examiner—R. Bruce Breneman
Attorney, Agent, or Firm—Alexander J. McKillop; Dennis P. Santini; Lori F. Cuomo

[57] ABSTRACT

A process for the selective surface dealumination of a zeolite having a Constraint Index greater than 1 by contacting the zeolite with dicarboxylic acid, such as oxalic acid.

22 Claims, No Drawings

SELECTIVE SURFACE DEALUMINATION OF ZEOLITES USING DICARBOXYLIC ACID

CROSS-REFERENCE TO RELATED APPLICATIONS

This application is related by subject matter to copending applications Ser. Nos. 07/828,624, filed Jan. 31, 1992, and 07/881,278, filed May 11, 1992.

FIELD OF THE INVENTION

This application is directed to a process for the selective surface dealumination of zeolites having a Constraint Index greater than 1 by contacting with dicarboxylic acid.

BACKGROUND OF THE INVENTION

Zeolitic materials, both natural and synthetic, have been demonstrated to have catalytic properties for various types of hydrocarbon conversion and chemical processing. It is often advantageous to dealuminate these materials in order to improve their process performance. Performance measures include product selectivity, product quality and catalyst stability.

Conventional techniques for zeolite dealumination include hydrothermal treatment, mineral acid treatment with HCl, $HNO_3$, and $H_2SO_4$, and chemical treatment with $SiCl_4$ or EDTA. The treatments, however, do not exhibit selectivity to the zeolite crystal surface.

U.S. Pat. No. 3,442,795 to Kerr et al. describes a process for preparing highly siliceous zeolite-type materials from crystalline aluminosilicates by means of a solvolysis, e.g. hydrolysis, followed by a chelation. In this process, the acid form of a zeolite is subjected to hydrolysis, to remove aluminum from the aluminosilicate. The aluminum can then be physically separated from the aluminosilicate by the use of complexing or chelating agents such as ethylenediaminetetraacetic acid or carboxylic acid, to form aluminum complexes that are readily removable from the aluminosilicate. The examples are directed to the use of EDTA to remove alumina.

EP 0 259 526 B1 discloses the use of dealumination in producing ECR-17. The preferred dealumination method involves a combination of steam treatment and acid leaching, or chemical treatments with silicon halides. The acid used is preferably a mineral acid, such as HCl, $HNO_3$ or $H_2SO_4$, but may also be weaker acids such as formic, acetic, citric, oxalic, tartaric acids and the like.

U.S. Pat. No. 4,388,177 discloses modifying the shape selectivity of natural ferrierite by treating with oxalic acid to impart catalytic activity.

U.S. Pat. No. 4,088,605 discloses a crystalline aluminosilicate zeolite containing an aluminum-free outer shell prepared by initiating the crystallization in a crystallization medium and then altering the crystallization medium to eliminate the aluminum therein. This can be accomplished by a total replacement of the reaction mixture or by complexing from the original reaction mixture any remaining aluminum ion with reagents such as gluconic acid, tartaric acid, nitrilotriacetic acid or EDTA.

Non-selective reactions on the surface acid sites of the zeolite are generally undesirable. These non-selective reactions on often lead to lower product yield and/or inferior product characteristics. To minimize the incidence of undesirable reactions occuring on the surface of the zeolite catalyst, methods have been used to reduce or eliminate surface acidity by extraction with bulky reagents or by surface poisoning.

Zeolite modification by exchange and similar technology with large cations such as $N^+$ and $P^+$ and large branched compounds such as polyamines and the like is described in U.S. Pat. No. 4,101,595. Bulky phenolic and silicating zeolite surface modifying agents are described in U.S. Pat. Nos. 4,100,215 and 4,002,697, respectively. The surface acidity of the zeolite can be eliminated or reduced by treatment with bulky dialkylamine reagents as described in U.S. Pat. Nos. 4,520,221 and 4,568,786.

U.S. Pat. No. 4,716,135 discloses zeolite catalysts can be surface inactivated by cofeeding a sterically hindered base or organophosphorus compound. U.S. Pat. No. 5,080,878 discloses modifying a crystalline aluminosilicate zeolite with a fluorosilicate salt to extract surface zeolite aluminum which is replaced by silicon. U.S. Pat. No. 5,043,307 discloses modifying a crystalline aluminosilicate zeolite by steaming as synthesized zeolite containing organic template material and then contacting the zeolite in the ammonium, alkali metal, or hydrogen form with a dealuminizing agent which forms a water soluble complex with aluminum. These methods, however, often increase the complexity and operability of the process.

Therefore, it is an object of the present invention to provide a process for surface selective dealumination of crystalline aluminosilicate zeolites. It is a further object of the present invention to minimize non-selective reactions on the surface acid sites of the crystalline aluminosilicate zeolites. It is a further object of the present invention to improve process performance of crystalline aluminosilicate zeolites.

SUMMARY OF THE INVENTION

Limiting surface acidity is desirable for preventing undesired reactions on the zeolite surface which are not subject to the shape selective constraints imposed on those reactions occurring within the zeolite interior. However reducing the surface acidity will generally effect a reduction in overall activity of the zeolite. The present invention relates to dicarboxylic acid treatment of zeolites with a C.I. >1 resulting in a reduction in surface acidity without a significant reduction in overall activity.

The invention therefore includes a process for the selective surface dealumination of a zeolite having a Constraint Index greater than 1 comprising contacting the zeolite with dicarboxylic acid for a sufficient time to effect at least about a 40% reduction in surface acidity with less than about 50% overall dealumination.

DETAILED DESCRIPTION OF THE INVENTION

The process of the invention is useful for the selective surface dealumination of a zeolite having a Constraint Index greater than 1.

The method by which Constraint Index is determined is described fully in U.S. Pat. No. 4,016,218, incorporated herein by reference for details of the method. Constraint Index (CI) values for some typical zeolites including some which are suitable in the process of this invention are:

| | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C. |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites in which the dicarboxylic acid treatment of the present invention to selectively dealuminate the surface of zeolites is effective. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore by appreciated that it may be possible to select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 5 or less, depending on the temperature employed during the test method within the range of 290° C. to about 538° C., with accompanying conversion between 10% and 60%, the CI may vary within the indicated range of 5 or less. Accordingly, it will be understood to those skilled in the art that the CI as utilized herein, while affording a highly useful means for characterizing the zeolites of interest, is approximate taking into consideration the manner of its determination including the possibility in some instances of compounding variable extremes. However, in all instances, at a temperature within the above-specified range of 290° C. to about 538° C., the CI will have a value for any given zeolite of interest herein of not greater than about 5 and preferably not greater than about 3.

Some zeolite catalysts which are useful in the process of this invention include zeolites ZSM-5, ZSM-11, ZSM-22, ZSM-23, ZSM-35, MCM-22, and MCM-49.

ZSM-5 is described in U.S. Pat. No. 3,702,886; ZSM-11 is described in U.S. Pat. No. 3,709,979; ZSM-22 is described in U.S. Pat. No. 4,556,477; ZSM-23 is described in U.S. Pat. No. 4,076,842; ZSM-35 is described in U.S. Pat. No. 4,016,245; and MCM-22 is described in U.S. Pat. No. 4,954,325, the disclosures of which are incorporated herein by reference.

MCM-49 has a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than about 35, e.g. from 2 to less than about 35, usually from about 10 to less than about 35, more usually from about 15 to about 31. In the as-synthesized form, the material has a formula, on an anhydrous basis and in terms of moles of oxides per n moles of $YO_2$, as follows:

$$(0.1–0.6)M_2O:(1–4)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The crystalline MCM-49 material is thermally stable and in the calcined form exhibits high surface area (greater than 400 m$^2$/gm) and unusually large sorption capacity when compared to previously described materials such as calcined PSH-3 (U.S. Pat. No. 4,439,409) and SSZ-25 (U.S. Pat. No. 4,826,667 and European Patent Application 231,860) having similar X-ray diffraction patterns. To the extent desired, the original sodium cations of the as-synthesized material can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-49 material appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, I/Io × 100 |
|---|---|
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

The X-ray diffraction peak at 13.15±0.26 Angstrom Units (A) is usually not fully resolved for MCM-49 from the intense peak at 12.49±0.24, and is observed as a shoulder of this intense peak. For this reason, the precise intensity and position of the 13.15±0.26 Angstroms peak are difficult to determine within the state range.

In its calcined form, the crystalline MCM-49 material transforms to a single crystal phase with little or no detectable impurity crystal phases having an X-ray diffraction pattern which is not readily distinguished from that of MCM-22, but distinguishable from the patterns of other known crystalline materials. The X-ray diffraction pattern of the calcined form of MCM-49 includes the lines listed in Table II below:

TABLE II

| Interplanar d-Spacing (A) | Relative Intensity, I/Io × 100 |
|---|---|
| 12.41 ± 0.24 | vs |
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, I/I$_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60–100), s=strong (40–60), m=medium (20–40) and w=weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-49 with similar materials, e.g. MCM-22 and PSH-3.

The significance of differences in the X-ray diffraction patterns of these materials can be explained from a knowledge of the structures of the materials. MCM-22 and PSH-3 are members of an unusual family of materials because, upon calcination, there are changes in the X-ray diffraction pattern that can be explained by a significant change in one axial dimension. This is indicative of a profound change in the bonding within the materials and not a simple loss of the organic material. The precursor members of this family can be clearly distinguished by X-ray diffraction from the calcined members. An examination of the X-ray diffraction patterns of both precursor and calcined forms shows a number of reflections with very similar position and intensity, while other peaks are different. Some of these differences are directly related to the changes in the axial dimension and bonding.

The as-synthesized MCM-49 has an axial dimension similar to those of the calcined members of the family and, hence, there are similarities in their X-ray diffraction patterns. Nevertheless, the MCM-49 axial dimension is different from that observed in the calcined materials. For example, the changes in axial dimensions in MCM-22 can be determined from the positions of peaks particularly sensitive to these changes. Two such peaks occur at ~13.5 Angstroms and ~6.75 Angstroms in precursor MCM-22, at ~12.8 Angstroms and ~6.4 Angstroms in as-synthesized MCM-49, and at ~12.6 Angstroms and ~6.30 Angstroms in the calcined MCM-22. Unfortunately, the ~12.8 Angstroms peak in MCM-49 is very close to the intense ~12.4 Angstroms peak observed for all three materials, and is frequently not fully separated from it. Likewise, the ~12.6 Angstroms peak of the calcined MCM-22 material is usually only visible as a shoulder on the intense ~12.4 Angstroms peak. Table I lists all diffraction peaks characteristic of MCM-49.

When used as a catalyst, the crystalline MCM-49 material may be subjected to treatment to remove part or all of any organic constituent. The crystalline material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g. aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline MCM-49 material can be transformed to another form by thermal treatment. This thermal treatment is generally performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g. hydrocarbon, conversion reactions. Non-limiting examples of such reactions include those for which MCM-22 may be used as catalyst. Incorporated herein by reference for the descriptions of those particular conversion reactions are U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422.

The crystalline MCM-49 material, when employed either as an adsorbent or as a catalyst in an organic compound conversion process, should be dehydrated, at least partially. This can be done by heating to a temperature in the range of 200° C. to about 370° C. in an atmosphere such as air, nitrogen, etc. and at atmospheric, subatmospheric or superatmospheric pressures for between 30 minutes and 48 hours. Dehydration can also be performed at room temperature merely by placing the MCM-49 in a vacuum, but a longer time is required to obtain a sufficient amount of dehydration.

The crystalline MCM-49 material can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, directing agent (R), and water, said reaction mixture having a composition, in terms of mole ratios of oxides, within the following ranges:

| Reactants | Useful | Preferred |
|---|---|---|
| $YO_2/X_2O_3$ | 12 to <35 | 18 to 31 |
| $H_2O/YO_2$ | 10 to 70 | 15 to 40 |
| $OH^-/YO_2$ | 0.05 to 0.50 | 0.05 to 0.30 |
| $M/YO_2$ | 0.05 to 3.0 | 0.05 to 1.0 |
| $R/YO_2$ | 0.2 to 1.0 | 0.3 to 0.5 |

In the MCM-49 synthesis method, if more than one X component is present, at least one must be present such that the $YO_2/X_2O_3$ molar ratio thereof is less than about 35. For example, if aluminum oxide and gallium oxide components are used in the reaction mixture, at least one of the $YO_2/Al_2O_3$ and $YO_2/Ga_2O_3$ molar ratios must be less than about 35. If only aluminum oxide has been added to the reaction mixture as a source of X, the $YO_2/Al_2O_3$ ratio must be less than about 35.

In the MCM-49 synthesis method, the source of $YO_2$ must be comprised predominately of solid $YO_2$, for example at least about 30 wt.% solid $YO_2$ in order to obtain the crystal product of the invention. Where $YO_2$ is silica, the use of a silica source containing at least about 30 wt.% solid silica, e.g. Ultrasil (a precipitated, spray dried silica containing about 90 wt.% silica) or HiSil (a precipitated hydrated $SiO_2$ containing about 87 wt.% silica, about 6 wt.% free $H_2O$ and about 4.5 wt.% bound $H_2O$ of hydration and having a particle size of about 0.02 micron) favors crystalline MCM-49 formation from the above mixture. Preferably, therefore, the $YO_2$, e.g. silica, source contains at least about 30 wt.% solid $YO_2$, e.g. silica, and more preferably at least about 40 wt.% solid $YO_2$, e.g. silica.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

Crystallization of the crystalline MCM-49 material can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of MCM-49 may be facilitated by the presence of at least 0.01 percent, preferably 0.10 percent and still more preferably 1 percent, seed crystals (based on total weight) of crystalline product. Useful seed crystals include MCM-22 and/or MCM-49.

The MCM-49 can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

Prior to or following the selective surface dealumination process of the present invention, it may be desirable to incorporate the zeolites with another material resistant to the temperature and other conditions employed in the process. Such matrix materials include synthetic or natural substances as well as inorganic materials such as clay, silica and/or metal oxides, such as titania or zirconia. The latter may be either naturally occurring or in the form of gelatinous precipitates or gels including mixtures of silica and metal oxides. Naturally occurring clays which can be composited with the zeolite include those of the montmorillonite and kaolin families. These clays can be used in the raw state as originally mined or initially subjected to calcination, acid treatment or chemical modification. These materials, i.e. clays, oxides, etc., function, in part, as binders for the catalyst.

In addition to the foregoing materials, the zeolites may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

Suitable dicarboxylic acids for use in the process of this invention include oxalic, malonic, succinic, glutaric, adipic, maleic, phthalic, isophthalic, terephthalic, fumaric, tartaric or mixtures thereof. Oxalic acid is preferred. The dicarboxylic acid may be used in solution, such as an aqueous dicarboxylic acid solution.

Generally, the acid solution has a concentration in the range from about 0.01 to about 4M. Preferably, the acid solution concentration is in the range from about 1 to about 3M.

The dicarboxylic acid is generally in a volume solution to volume catalyst ratio of at least about 1:1, preferably at least about 4:1.

Treatment time with the dicarboxylic acid solution is as long as required to provide the desired dealumination. Generally the treatment time is at least about 10 minutes. Preferably, the treatment time is at least about 1 hour.

The treatment temperature is generally in the range from about 32.F to about reflux. Preferably, the treatment temperature is from about 60° F. to about 200° F., and more preferably from about 120° F. to about 180° F.

More than one dicarboxylic acid treatment step may be employed in the process of the present invention for enhanced surface dealumination.

The dicarboxylic acid treatment of this invention may also be combined with other conventional dealumination techniques, such as steaming and chemical treatment.

The dicarboxylic acid selectively dealuminates the surface acid sites of zeolites with a C.I. >1. The presence of surface acid sites, or surface acidity, is determined by the dealkylation of tri-tertbutylbenzene (TTBB), a bulky molecule that can only react with the acid sites on the zeolite crystal surface.

Dealkylation of TTBB is a facile, reproducible method for measuring surface acidity of catalysts. External surface activity can be measured exclusive of internal activity for zeolites with pore diameters up to and including faujasite. As a test reaction dealkylation of TTBB occurs at a constant temperature in the range of from about 25 to about 300° C., and preferably in the range of from about 200 to about 260° C.

The experimental conditions for the test used herein include a temperature of 200° C. and atmospheric pressure. The dealkylation of TTBB is carried out in a glass reactor (18 cm×1 cm OD) containing an 8 gm 14/30 mesh Vycor chip preheater followed by 0.1 gm catalyst powder mixed with Vycor chips. The reactor is heated to 200° C. in 30 cc/gm nitrogen for 30 minutes to remove impurities from the catalyst sample. Ten gm/hr of TTBB dissolved in toluene (7% TTBB) is injected into the reactor. The feed vaporizes as it passes through the preheator and is vapor when passing over the catalyst sample. After equilibrium is reached the nitrogen is switched to 20 cc/min hydrogen. The test is then run for about 30 minutes with the reaction products collected in a cold trap.

The reaction products are analyzed by gas chromatography. The major dealkylation product is di-t-butylbenzene (DTBB). Further dealkylation to t-butylbenzene (TBB) and benzene (B) occurs but to a lesser extent.

Conversion of TTBB is calculated on a molar carbon basis. Dealkylation product weight % are each multiplied by the appropriate carbon number ratio to convert to the equivalent amount of TTBB, i.e. DTBB×18/14, TBB×18/10 and B×18/6. These values are then used in the following conversion equation where asterisks indicate adjustment to the equivalence.

$$\% \text{ Conversion} = \frac{DTBB^* + TBB^* + B^*}{TTBB + DTBB^* + TBB^* + B^*}$$

In addition, thermal background experiments using reactors filled with vycor chips only show no TTBB conversion due to Vycor chips or other reactor components.

The overall cracking activity is measured by Alpha Value. When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The dicarboxylic acid treatment of this invention results in less than about 50% overall dealumination, preferably less than about 20% overall dealumination, and more preferably less than about 10% overall dealumination with greater than about 40% reduction in surface acidity, preferably greater than about 50% reduction in surface acidity, and more preferably greater than about 60% reduction in surface acidity.

The following examples illustrate the process of the present invention.

EXAMPLE 1

Sixty-five parts by weight of ZSM-35 synthesized in accordance with U.S. Pat. No. 4,016,245, incorporated herein by reference, and having a Constraint Index of 4.5 is mixed with 35 parts of $SiO_2$ on a dry basis. The mixture is dry mulled and formed into 1/16" cylindrical extrudates. The extrudates are dried at 250° F. for 8 hours, activated and calcined in air at 1000° F. for 3 hours. The resulting catalyst referred to henceforth as Catalyst A has the following properties:

| Alpha Value | 102 |
|---|---|
| Surface Acidity | 18 |
| $Al_2O_3$, wt % | 5.7 |

EXAMPLE 2

A sample of Catalyst A as set forth in Example 1 is treated with 2M oxalic acid at 160° F. for 1 hour. The treated sample is washed with water, dried at 250° F. for 8 hours and calcined in air at 1000° F. for 3 hours. The treatment results in 4% overall dealumination with 44% reduction in surface acidity. The oxalic acid treated catalyst has the following properties:

| Alpha Value | 92 |
|---|---|
| Surface Acidity | 10 |
| $Al_2O_3$, wt % | 5.5 |

EXAMPLE 3

Sixty-five parts by weight of ZSM-23 synthesized in accordance with U.S. Pat. No. 4,076,842, incorporated herein by reference, and having a Constraint Index of 9.1, is mixed with 35 parts by weight of $SiO_2$ on a dry basis. The mixture is dry mulled and formed into 1/16" cylindrical extrudates. The extrudates are dried at 250° F. for 8 hours, activated and calcined in air at 1000° F. for 3 hours. The resulting catalyst henceforth referred to as Catalyst B has the following properties:

| Alpha Value | 25 |
|---|---|
| Surface Acidity | 4.6 |
| Al$_2$O$_3$, wt % | 1.1 |

EXAMPLE 4

A sample of Catalyst B as set forth in Example 3 is treated with 2M oxalic acid at 160° F. for 1 hour. The treated sample is washed with water, dried at 250° F. for 8 hours and calcined in air at 1000° F. for 3 hours. The treatment results in 18% overall dealumination with 50% reduction in surface acidity. The oxalic acid treated catalyst has the following properties:

| Alpha Value | 26 |
|---|---|
| Surface Acidity | 2.1 |
| Al$_2$O$_3$, wt % | 0.9 |

EXAMPLE 5

Sixty-five parts by weight ZSM-5 synthesized in accordance with U.S. Pat. No. 3,702,886, incorporated herein by reference, and having a Constraint Index of 6.0, is mixed with 35 parts by weight of SiO$_2$ on a dry basis. The mixture is dry mulled and formed into 1/16" cylindrical extrudates. The extrudates are dried at 250° F. for 8 hours, activated and calcined in air at 1000° F. for 3 hours. The resulting catalyst henceforth referred to as Catalyst C has the following properties:

| Alpha Value | 275 |
|---|---|
| Surface Acidity | 18 |
| Al$_2$O$_3$, wt % | 1.6 |

EXAMPLE 6

A sample of catalyst C as set forth in Example 5 is treated with 2M oxalic acid at 160° F. for 1 hour. The treated sample is washed with water, dried at 250° F. for 8 hours and calcined in air at 1000° F. for 3 hours. The treatment results in 6% overall dealumination with 94% reduction in surface acidity. The oxalic acid treated catalyst has the following properties:

| Alpha Value | 258 |
|---|---|
| Surface Acidity | <1 |
| Al$_2$O$_3$, wt % | 1.5 |

EXAMPLE 7

This is a comparative example which demonstrates the dealumination of large-pore zeolites with a C.I. <1 is non-selective to the zeolite crystal surface and affects the overall activity as measured by Alpha Value.

Zeolite Beta synthesized in accordance with U.S. Pat. Nos. 3,308,069 and Re 28,341, incorporated herein by reference, and having a Constraint Index of 0.6. Organics are removed by treating in N$_2$ at 650° F. for 3 hours followed by air calcination at 1000° F. for 6 hours. The calcined zeolite henceforth referred to as catalyst D has the following properties:

| Alpha Value | 400 |
|---|---|
| Al$_2$O$_3$, wt % | 4.6 |
| Surface Acidity | 59 |

EXAMPLE 8

A sample of catalyst D as set forth in Example 7 is treated with a 2M solution of oxalic acid at a solution to catalyst ratio of 16 to 1. Treatment is conducted at 160° F. for 1 hour. The treated catalyst is dried at 250° F. overnight. The dried catalyst is calcined in air at 1000° F. for 3 hours. The treatment results in 91% overall dealumination in addition to the 92% reduction in surface acidity. The oxalic acid treated catalyst has the following properties:

| Alpha Value | 11 |
|---|---|
| Al$_2$O$_3$, wt % | .40 |
| Surface Acidity | 7 |

Changes and modifications in the specifically described embodiments can be carried out without departing from the scope of the invention which is intended to be limited only by the scope of the appended claims.

What is claimed is:

1. A process for the selective surface dealumination of a zeolite having a Constraint Index greater than 1 comprising contacting the zeolite with dicarboxylic acid for a sufficient time to effect at least about a 40% reduction in surface acidity with less than about 50% overall dealumination.

2. The process of claim 1 wherein said reduction in surface activity is determined by dealkylation of tri-tert-butylbenzene.

3. The process of claim 1 wherein said zeolite having a Constraint Index greater than 1 is selected from the group consisting of ZSM-5, ZSM-11, ZSM-22, ZSM-23, ZSM-35, MCM-22, and MCM-49.

4. The process of claim 1 wherein said zeolite is unbound.

5. The process of claim 1 wherein said zeolite is bound with an inorganic oxide binder prior to said selective surface dealumination.

6. The process of claim 1 wherein said surface acidity is reduced by at least about 50%.

7. The process of claim 1 wherein said surface acidity is reduced by at least about 60%.

8. The process of claim 1 wherein said overall dealumination is less than about 20%.

9. The process of claim 1 wherein said overall dealumination is less than about 10%.

10. The process of claim 1 wherein said zeolite is ZSM-35.

11. The process of claim 1 wherein said dicarboxylic acid is in solution.

12. The process of claim 11 wherein said solution of dicarboxylic acid is at a volume ratio of solution to catalyst containing said zeolite of at least about 1:1.

13. The process of claim 1 wherein said dicarboxylic acid is an aqueous dicarboxylic acid solution.

14. The process of claim 1 wherein said dicarboxylic acid is in a concentration in the range of from about 0.01M to about 4M.

15. The process of claim 1 wherein said dicarboxylic acid is selected from the group consisting of oxalic, malonic, succinic, glutaric, adipic, maleic, phthalic, isophthalic, terephthalic, fumaric, tartaric and mixtures thereof.

16. The process of claim 3 wherein said dicarboxylic acid is oxalic acid.

17. The process of claim 1 wherein said contacting is for a time of at least about 10 minutes.

18. The process of claim 1 wherein said contacting is at a temperature in the range of from about 60° F. to about 200° F.

19. A process for the selective surface dealumination of a zeolite having a Constraint Index greater than 1 comprising contacting the zeolite with oxalic acid for a sufficient time to effect at least about a 40% reduction in surface acidity with less than about 50% overall dealumination.

20. A process for the selective surface dealumination of a zeolite having a Constraint Index greater than 1 comprising contacting the zeolite with dicarboxylic acid for a time in the range of about 10 minutes to about 1 hour to effect at least about a 40% reduction in surface acidity with less than about 50% overall dealumination.

21. A process for the selective surface dealumination of a zeolite having the structure of ZSM-23 comprising contacting the zeolite with dicarboxylic acid for a sufficient time to effect at least about a 40% reduction in surface acidity with less than about 50% overall dealumination.

22. A process for the selective surface dealumination of a zeolite having the structure of ZSM-5 comprising contacting the zeolite with dicarboxylic acid for a sufficient time to effect at least about a 40% reduction in surface acidity with less than about 50% overall dealumination.

* * * * *

UNITED STATES PATENT AND TRADEMARK OFFICE
CERTIFICATE OF CORRECTION

PATENT NO. : 5,242,676
DATED : September 7, 1993
INVENTOR(S) : Minas R. Apelian and Anthony S. Fung It is certified that error appears in the above-identified patent and that said Letters Patent is hereby corrected as shown below:

Column 12,
Claim 2, line 2, "activity" should be --acidity--

Signed and Sealed this

Third Day of May, 1994

Attest:

BRUCE LEHMAN

Attesting Officer

Commissioner of Patents and Trademarks